(12) United States Patent
Badylak

(10) Patent No.: US 8,409,625 B2
(45) Date of Patent: Apr. 2, 2013

(54) CONDITIONED DECELLULARIZED NATIVE TISSUES FOR TISSUE RESTORATION

(75) Inventor: Stephen F. Badylak, West Lafayette, IN (US)

(73) Assignee: ACell, Inc., Columbia, MD (US)

( * ) Notice: Subject to any disclaimer, the term of this patent is extended or adjusted under 35 U.S.C. 154(b) by 762 days.

(21) Appl. No.: 12/351,757

(22) Filed: Jan. 9, 2009

(65) Prior Publication Data

US 2009/0118166 A1 May 7, 2009

Related U.S. Application Data

(63) Continuation of application No. 10/876,299, filed on Jun. 24, 2004, now abandoned.

(60) Provisional application No. 60/482,480, filed on Jun. 25, 2003, provisional application No. 60/538,385, filed on Jan. 21, 2004.

(51) Int. Cl.
    *A61K 35/12* (2006.01)
(52) U.S. Cl. ........................................ 424/574; 424/484
(58) Field of Classification Search ........................ None
    See application file for complete search history.

(56) References Cited

U.S. PATENT DOCUMENTS

| | | |
|---|---|---|
| 2,127,903 A | 8/1938 | Bowen |
| 3,562,820 A | 2/1971 | Braun |
| 4,439,521 A | 3/1984 | Archer et al. |
| 4,703,108 A | 10/1987 | Silver et al. |
| 4,743,552 A | 5/1988 | Friedman et al. |
| 4,776,853 A | 10/1988 | Klement et al. |
| 4,801,299 A | 1/1989 | Brendel et al. |
| 4,829,000 A | 5/1989 | Kleinman et al. |
| 4,902,508 A | 2/1990 | Badylak et al. |
| 4,956,178 A | 9/1990 | Badylak et al. |
| 5,266,480 A | 11/1993 | Naughton et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,445,833 A | 8/1995 | Badylak et al. |
| 5,478,739 A | 12/1995 | Slivka et al. |
| 5,480,424 A | 1/1996 | Cox |
| 5,516,533 A | 5/1996 | Badylak et al. |
| 5,543,894 A | 8/1996 | Carolan |
| 5,554,389 A | 9/1996 | Badylak et al. |
| 5,573,784 A | 11/1996 | Badylak et al. |
| 5,618,312 A | 4/1997 | Yui et al. |
| 5,641,518 A | 6/1997 | Badylak et al. |
| 5,695,998 A | 12/1997 | Badylak et al. |
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,855,620 A | 1/1999 | Bishopric et al. |
| 5,866,414 A | 2/1999 | Badylak et al. |
| 5,866,415 A | 2/1999 | Villeneuve et al. |
| 5,869,041 A | 2/1999 | Vandenburgh |
| 5,885,619 A | 3/1999 | Patel et al. |
| 5,891,617 A | 4/1999 | Watson et al. |
| 5,899,936 A | 5/1999 | Goldstein |
| 5,916,266 A | 6/1999 | Yui et al. |
| 6,022,887 A | 2/2000 | Gasper et al. |
| 6,051,750 A | 4/2000 | Bell |
| 6,087,157 A | 7/2000 | Badylak et al. |
| 6,096,347 A | 8/2000 | Geddes et al. |
| 6,126,686 A | 10/2000 | Badylak et al. |
| 6,171,344 B1 | 1/2001 | Atala |
| 6,206,931 B1 | 3/2001 | Cook et al. |
| 6,322,593 B1 | 11/2001 | Pathak et al. |
| 6,376,244 B1 | 4/2002 | Atala |
| 6,432,712 B1 | 8/2002 | Wolfinbarger, Jr. et al. |
| 6,454,804 B1 | 9/2002 | Ferree |
| 6,455,311 B1 | 9/2002 | Vacanti |
| 6,479,064 B1 | 11/2002 | Atala |
| 6,485,723 B1 | 11/2002 | Badylak et al. |
| 6,485,969 B1 | 11/2002 | Asem et al. |
| 6,572,650 B1 | 6/2003 | Abraham et al. |
| 6,576,265 B1 | 6/2003 | Spievack |
| 6,579,538 B1 | 6/2003 | Spievack |
| 6,783,776 B2 | 8/2004 | Spievack |
| 6,849,273 B2 | 2/2005 | Spievack |
| 6,852,339 B2 | 2/2005 | Spievack |

(Continued)

FOREIGN PATENT DOCUMENTS

DE 198 28 726 1/1999
EP 0 773 033 5/1997

(Continued)

OTHER PUBLICATIONS

Seikagaku jiten [Biochemistry Dictionary] (2$^{nd}$ Edition), Nov. 22, 1990, pp. 324-325 (English translation attached).

(Continued)

*Primary Examiner* — Allison Ford
(74) *Attorney, Agent, or Firm* — Burns & Levinson, LLP

(57) ABSTRACT

The invention provides a composition conditioned for the remodeling, restoration, repair, or replacement of tissue within a host. The composition is conditioned by culturing cells on the matrix and/or by exposing the cultured cells or matrix to one or more stressors.

15 Claims, No Drawings

U.S. PATENT DOCUMENTS

| | | | |
|---|---|---|---|
| 6,861,074 | B2 | 3/2005 | Spievack |
| 6,869,619 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 2002/0061587 | A1* | 5/2002 | Anversa .................... 435/366 |
| 2002/0115208 | A1 | 8/2002 | Mitchell et al. |
| 2002/0172705 | A1 | 11/2002 | Murphy et al. |
| 2003/0133916 | A1 | 7/2003 | Spievack |
| 2003/0148510 | A1 | 8/2003 | Mitrani |
| 2003/0211130 | A1 | 11/2003 | Sanders et al. |
| 2004/0043006 | A1 | 3/2004 | Badylak et al. |
| 2004/0175366 | A1 | 9/2004 | Badylak |
| 2004/0176855 | A1 | 9/2004 | Badylak |

FOREIGN PATENT DOCUMENTS

| | | |
|---|---|---|
| WO | 93/00441 | 1/1993 |
| WO | 95/24873 | 9/1995 |
| WO | 96/01833 | 1/1996 |
| WO | 96/32905 | 10/1996 |
| WO | 97/17038 | 5/1997 |
| WO | 98/22158 | 5/1998 |
| WO | 98/25545 | 6/1998 |
| WO | 98/25546 | 6/1998 |
| WO | 98/25637 | 6/1998 |
| WO | 98/46165 | 10/1998 |
| WO | 00/15765 | 3/2000 |
| WO | 01/45765 | 6/2001 |
| WO | 02/14480 | 2/2002 |
| WO | 03/043674 | 5/2003 |

OTHER PUBLICATIONS

Iwanami Koza Gendaiigaku no Kiso 3 Jintai no Naritachi [Iwanami Lecture, Basics of Contemporary Medicine 3 Structure of the Human Body], Nov. 20, 1998, pp. 16-18 (English translation attached).

Ansel et al., Journal of Clinical Investigation, 1993, vol. 92, No. 2, pp. 671-678.

Badylak et al., "Endothelial Cell Adherence to Small Intestinal Submucosa: An Acellular Bioscaffold," Biomaterials 20:2257-2264 (1999).

Badylak et al., "Marrow-derived Cells Populate Scaffolds Composed of Xenogeneic Extracellular Matrix," Exptl. Hematol., 29:1310-1318 (2001).

Badylak et al., "Resorbable Bioscaffold for Esophageal Repair in a Dog Model," J. Pediatr. Surg., 35:1097-1103 (2000).

Badylak et al. "Small intestine submucosa: a substrate for in vitro cell growth," J. Biomat. Science 9:863-878 (1998).

Chaudhuri et al., "Detection and Gradation of Oriented Texture," Pattern Recognition Letters, 14(2): 147-153 (1993).

Chekanov et al., "Electrical Stimulation Promotes Angiogenesis in a Rabbit Hind-limb Ischemia Model," Vasc. Endovascular Surg. 36:357-66 (2002).

Dahms et al., "Bladder Acellular Matrix Graft in Rats: Its Neurophysiologic Properties and mRNA Expression of Growth Factors TGF-a and TGF-b," Neurourology and Urodynamics 17:37-54 (1998).

Dahms et al, "Composition and biomechanical properties of the bladder acellular matrix graft: comparative analysis in rat, pig and human," British Journal of Urology 82:411-419 (1998).

Dahms et al., "Free Ureteral Replacement in Rats: Regeneration of Ureteral Wall Components in the Acellular Matrix Graft," Urology 50(5) 818-825 (1997).

Evans et al., "Electrical Stimulation With Bone and Wound Healing," Clin. Podiatr. Med. Surg. 18:79-95 (2001).

Hadlock et al., "A New Artificial Nerve Graft Containing Rolled Schwann Cell Monolayers," Microsurgery 21:96-101 (2001).

Kanazawa et al., "The Oscillation Frequency of a Quartz Resonator in Contract with a Liquid," Anal. Chim. Acta, 175:99-105 (1985).

Lakey et al., "Improved Islet Survival and In Vitro Function Using Small Intestinal Submucosa," Transplantation Proceedings 30:383 (1998).

Lindberg et al., "Porcine small intestinal submucosa (SIS): a bioscaffold supporting in vitro primary human epidermal cell differentiation and synthesis of basement membrane proteins," Burns, 27:254-266 (2001).

Liu et al., "Statistical Analysis of Collagen Alignment in Ligaments by Scale-Space Analysis," IEEE Transactions on Biomedical Engineering 38:580-588 (1991).

McGuire et al., "Role of Extracellular Matrix in Regulating Fenestrations of Sinusoidal Endothelial Cells Isolated From Normal Rat Liver," Hepatology 15:989-997 (1992).

McMillan et al., Macromolecules, 2000, vol. 33, pp. 4809-4821.

Mori et al., "Defenestrations of the Sinusoidal Endothelial Cell in a Rat Model of Cirrhosis," Hepatology 17:891-897 (1993).

Pariente et al., "In Vitro Biocompatibility Assessment of Naturally Derived and Synthetic Biomaterials using Normal Urothelial Cells," J. Biomed. Mater. Res. 55:33-39 (2001).

Peel et al., "Formation of a SIS-cartilage composite graft in vitro and its use in the repair of articular cartilage defects," Tissue Eng. 4:143-155 (1998).

Piechota et al., "Functional rat bladder regeneration through xenotransplantation of the bladder acellular matrix graft," British Journal of Urology 81:548-559 (1998).

Piechota et al., "In Vitro Functional Properties of the Rat Bladder Rengerated by the Bladder Acellular Matrix Graft," Journal of Urology 159:1717-1724 (1998).

Probst et al., "Homologous bladder augmentation in dog with the bladder acellular matrix graft," BJU International 85:362-371 (2000).

Rosenthal et al., "The Mucosal Invasion Model," Arch. Otolaryngol. Head Neck Surgery 127:1467-1470 (2001).

Rupp, et al., "Integrins in Vascular Development," Circ. Res. 89:566-72 (2001).

Sherratt et al., "Theoretical Models of Wound Healing: Past Successes and Future Challenges," C. R. Biol. 325:557-64 (2002).

Sisken et al., "Prospects on Clinical Applications of Electrical Stimulation for Nerve Regeneration," J. Cell Biochem. 51L404-9 (1993).

Sutherland et al., (1996), "Regeneration of Bladder Urothelium, Smooth Muscle, Blood Vessels, and Nerves Into an Acellular Tissue Matrix," Journal of Urology, 156(2): 571-577.

Tonnesen et al., "Angiogenesis in Wound Healing," J. Investig. Dermatol. Symp. Proc. 5:40-6 (2000).

van Hinsbergh et al., "Role of Fibrin Matrix in Angiogenesis," Ann. N.Y. Acad. Sci. 936:426-37 (2001).

van Hinsbergh et al, "The Endothelium: Vascular Control of Haemostatis," Eur. J. Obstet. Gynecol. Reprod. Biol. 95:198-201 (2001).

Voytik-Harbin et al., "Three-dimensional imaging of extracellular matrix and extracellular matrix-cell interactions," Methods Cell Biol. 63-583-597 (2001).

Weizmann et al., "Amplified Detection of DNA and Analysis of Single-base Mismatches by the Catalyzed Deposition of Gold on Au-nanoparticles," Analyst 126:1502-1504 (2001).

Whittaker et al., "Demonstration of Quantitative Fabric Analysis of Tendon Collagen Using Two-Dimensional Polarized Light Microscopy," Matrix 11:56-62 (1991).

Whittaker et al., "Quantitative Assessment of Myocardial Collagen with Picrosirius Red Staining and Circularly Polarized Light," Basic Research in Cardiology 89:397-410 (1994).

Yoo et al., "Bladder Augmentation Using Allogenic Bladder Submucosa Seeded with Cells," Urology 51(2):221-225 (1998).

* cited by examiner

CONDITIONED DECELLULARIZED NATIVE TISSUES FOR TISSUE RESTORATION

RELATED APPLICATIONS

This application is a continuation of U.S. patent application Ser. No. 10/876,299, filed Jun. 24, 2004, which claims priority to and the benefit of U.S. Provisional Patent Application No. 60/482,480, filed Jun. 25, 2003, and U.S. Provisional Patent Application No. 60/538,385, filed Jan. 21, 2004, the contents of each of which are incorporated by reference herein.

FIELD OF THE INVENTION

The present invention relates to compositions comprising matrices that are conditioned for remodeling, replacement, restoration or repair of tissue within a host, methods of making and methods of using the compositions.

BACKGROUND OF THE INVENTION

Tissue graft constructs, such as regenerative scaffolds, are commonly utilized in tissue engineering applications to repair, replace, restore and/or remodel damaged or diseased tissue. These tissue scaffolds often include matrices, for example, a naturally occurring extracellular matrix (ECM), to provide structure to the scaffold. Naturally occurring ECM is a mixture of structural and functional molecules arranged within a complex three-dimensional ultrastructure that surrounds and supports cells that are found within tissues and organs. Alternatively, a matrix may be manufactured from structural or functional components of a naturally occurring ECM, such as collagen. Naturally occurring ECMs are composed of both structural and functional biologically active molecules, including cytokines and growth factors, which play an important role in replication, differentiation, maturation and organization of cells in contact with the matrix.

The composition and structure of a naturally occurring ECM is a function of age of the host, location of the ECM within specific tissues and organs, and the demands placed upon the ECM as a result of environmental stressors. For example, naturally occurring musculotendinous ECM becomes stronger as a result of collagen deposition and collagen fiber reorganization in response to repeated uniaxial or multiaxial stress or compressive loading. Naturally occurring hepatic ECM shows increased concentration of laminin, fibronectin and collagen IV within hours of the onset of hypoxia. The naturally occurring ECM has been recognized as a critical component in the host response to tissue injury just as it is an essential element of normal tissue development.

Selected forms of the naturally occurring ECM, for example, ECM derived from the small intestinal submucosa (SIS), have been successfully used as a scaffold for tissue engineering applications in both pre-clinical animal studies and in human clinical applications. Experience with patients has suggested that the degree of success and the morphologic changes that occur within the scaffold over time are a direct result of local environmental stimuli, such as mechanical loading (rehabilitation), the viability of surrounding tissue, and the surrounding tissue pH and ionic concentrations. Although these scaffold compositions have provided a starting point for tissue engineering applications, there exists a need in the art for compositions that have improved ability to support the replication, differentiation, maturation and spatial organization of numerous cell types.

SUMMARY OF THE INVENTION

The present invention is based on the finding that compositions comprising matrices can be conditioned to augment the repair, replacement, remodeling, or restoration of a tissue in a patient. According to one aspect, the invention features a composition including a decellularized matrix. The matrix is conditioned by cells cultured on the matrix in vitro whereby the decellularized conditioned matrix has enhanced restorative, remodeling, replacement or repair properties when placed in contact with a tissue in a patient in need of restoration, remodeling, replacement or repair.

In one embodiment according to this aspect of the invention, the matrix comprises a naturally occurring extracellular matrix (ECM). In related embodiments, the ECM comprises at least a portion of tunica submucosa, at least a portion of epithelial basement membrane, or at least a portion of tunica propria. In other related embodiments according to this aspect of the invention, at least a portion of the ECM comprises dermis, subcutaneous tissue, pancreatic connective tissue, tissue harvested from the stomach, tissue harvested from the intestine, tissue harvested from the urinary bladder, tissue harvested from the skin or tissue harvested from a tissue comprising a mucous membrane.

In other embodiments of the invention, the matrix comprises a structural or functional component of a naturally occurring ECM, or the matrix comprises a degradation product of a structural or functional component of a naturally occurring ECM.

The cells for conditioning the matrix can be selected from the group consisting of a primary, secondary, and immortalized cell population. In one embodiment, the matrix conditioning cells are selected from the group consisting of fibroblasts, keratinocytes, astroglial cells, epithelial cells, endothelial cells, glial cells, neural cells, cells of the blood and precursors thereof, and hepatocyte and precursor cells thereof In a further embodiment, the matrix conditioning cells express a biologically active molecule of interest. The biologically active molecule of interest according to one embodiment comprises a protein, and in further embodiments, the protein is selected from the group consisting of angiogenin, angiopoietin-1, Del-1, acidic-fibroblast growth factor (aFGF), basic-fibroblast growth factor (bFGF), granulocyte colony-stimulating factor (G-CSF), granulocyte-macrophage colony-stimulating factor (GM-CSF), hepatocyte growth factor (HGF), Interleukin-8 (IL-8), leptin, placental growth factor (PlGF), platelet-derived endothelial cell growth factor (PD-ECGF), platelet-derived growth factor-BB (PDGF-BB), pleiotrophin (PTN), proliferin, transforming growth factor-alpha (TGF-alpha), transforming growth factor-beta (TGF-beta), tumor necrosis factor-alpha (TNF-alpha), vascular endothelial growth factor (VEGF), bone morphogenetic protein-2 (BMP-2) and stromal derived growth factor-1.

The protein according to one embodiment is a growth factor, and in related embodiments, the growth factor is an angiogenic growth factor or an osteogenic growth factor.

In another embodiment of the invention, the matrix conditioning cells are genetically-modified cells. In one embodiment, the genetically-modified cells are transfected cells comprising an exogenous nucleic acid and which express a protein of interest. In another embodiment, the genetically-modified cells are transfected with a nucleic acid that encodes a protein of interest. The genetically-modified cells can express a biologically active molecule of interest. In a related embodiment, the biologically active molecule of interest is a VEGF protein, a bFGF protein, a BMP protein, or a stromal derived growth factor-1 protein. In another related embodiment, the biologically active molecule of interest is a recombinant protein.

In a further embodiment, the matrix comprises a naturally occurring ECM and the ECM is harvested from a tissue of a vertebrate.

The tissue in need of restoration, remodeling, replacement or repair according to an embodiment of the invention comprises a tissue in a patient selected from the group consisting of bone, skin, heart, a tissue of the urogenital tract, a tissue of the gastrointestinal tract, nervous tissue, joint tissue and connective tissue.

In another embodiment, the matrix conditioning cells are exposed to at least one stressor. The at least one stressor can comprise hypoxia, hypercarbia, or an electrical current. In a further embodiment, the matrix is exposed to at least one stressor, and in a related embodiment the stressor comprises mechanical loading.

A further aspect of the invention generally involves a composition comprising a matrix conditioned by cells cultured on the matrix in vitro and by exposure to at least one stressor. The conditioned matrix has enhanced restorative, remodeling, replacement or repair properties when placed in contact with a tissue in need of restoration, remodeling, replacement or repair.

In one embodiment according to this aspect of the invention, the cells for conditioning the matrix are selected from the group consisting of fibroblasts, keratinocytes, astroglial cells, epithelial cells, endothelial cells, glial cells, neural cells, cells of the blood and precursors thereof, and hepatocyte and precursor cells thereof. In another embodiment, the matrix conditioning cells are autologous cells.

According to further embodiments of the invention, the at least one stressor comprises hypoxia, hypercarbia, electrical current, or mechanical loading. In another embodiment, the matrix conditioning cells express a biologically active molecule of interest, and in a related embodiment, the biologically active molecule of interest comprises a protein. In other embodiments, the matrix conditioning cells are genetically-modified cells and the genetically-modified cells express a biologically active molecule of interest. The biologically active molecule of interest can be a protein, and the protein can be a recombinant protein.

In another aspect, the invention features a method for inducing restoration, remodeling, replacement or repair of a tissue in a mammal. The method comprises providing a decellularized matrix, conditioning the matrix by culturing cells on the matrix in vitro, and decellularizing the matrix wherein the decellularized conditioned matrix induces restoration, remodeling, replacement or repair of the tissue.

In one embodiment of this aspect of the invention, the method includes the step of exposing the cells for conditioning the matrix to at least one stressor. In another embodiment, the method includes the step of exposing the matrix to at least one stressor. In a further embodiment, the tissue comprises a tissue selected from the group consisting of blood vessel tissue, heart tissue and bone tissue.

According to another embodiment, the cells for culturing the matrix express a biologically active molecule of interest. The biologically active molecule of interest can comprise a growth factor. In one embodiment, the biologically active molecule of interest comprises a VEGF protein, a stromal derived growth factor-1 protein, or a bone morphogenic protein.

In another embodiment, the matrix conditioning cells are genetically-modified cells, and in a related embodiment, the genetically-modified cells express a biologically active molecule of interest. In a further embodiment, the biologically active molecule of interest is a recombinant protein.

In yet another embodiment of the invention, the matrix is harvested from a tissue of a vertebrate.

A further aspect of the invention generally involves a composition for tissue replacement, repair, restoration, or remodeling in a patient. The composition comprises a decellularized matrix comprising a structural or functional component of a naturally occurring ECM, a degradation product of a structural or functional component of a naturally occurring ECM, or a combination thereof. The matrix is conditioned by culturing cells on the matrix in vitro. In one embodiment, the cells for conditioning the matrix are exposed to at least one stressor, and in another embodiment, the matrix is exposed to at least one stressor.

A further aspect of the invention features a composition comprising a matrix. The matrix is conditioned for tissue restoration, remodeling, replacement or repair by exposure to at least one stressor. In one embodiment, the stressor is an electric current.

By "biologically active molecule" is meant a molecule capable of causing an effect on, interaction with, or response from living matter.

The term "contacting" includes both direct and indirect contact, including fluid communication.

By "genetically modified cell" is meant a cell that includes an exogenous nucleic acid sequence.

By "exogenous nucleic acid sequence" is meant a nucleic acid which is introduced into a cell by transduction. The exogenous nucleic acid can be a gene which encodes a protein of interest or can be a nucleic acid sequence which alters the expression of a protein of interest, for example, upregulates the expression and production of the protein of interest. An exogenous nucleic acid sequence includes a nucleic acid that originates from a foreign species, or, if from the same species, is substantially modified from its native form in composition and/or genomic locus by deliberate human intervention.

By "transfection" is meant a process of introducing genes or gene fragments into cells.

By "transduced" is meant a process of inserting exogenous nucleic acids into cells. The insertion may, for example, be effected by transfection or transformation, viral infection, injection, transfection, gene bombardment, electroporation or any other means effective in introducing nucleic acids into cells. Following transduction, the exogenous nucleic acid is either integrated wholly or in part, to the cell's genome (DNA), or remains external to the cell's genome, thereby providing stably transduced or transiently transduced cells.

The term "primary cell" includes cells present in a suspension of cells isolated from a tissue source (prior to their being plated, i.e., attached to a tissue culture substrate such as a dish or flask), cells present in an explant derived from tissue, both of the previous types of cells plated for the first time, and cell suspensions derived from these plated cells. "Secondary cells" refers to cells at all subsequent steps in culturing. That is, the first time a plated primary cell is removed from the culture substrate and replated (passaged), it is referred to as a secondary cell, as are all cells in subsequent passages. By "immortalized cell" is meant a cell from an established cell line that is capable of cell division producing progeny that are capable of cell division in culture.

DETAILED DESCRIPTION OF THE INVENTION

The present invention is directed to a composition that is conditioned for replacing, repairing, restoring or remodeling tissue when implanted in a host. The composition includes a matrix derived from naturally occurring ECM or from structural or functional components of a naturally occurring ECM or their degradation products. The composition can be conditioned in various ways, including culturing cells on the matrix, exposing the cells and/or the matrix to altered environmental and/or physiological conditions, or a combination thereof. Culturing cells on the matrix and/or exposing the cultured cells and matrix to various stressors provides a conditioned composition with enhanced biological properties compared to matrices that are merely combined with various cells and not decellularized or combined with bioactive factors by chemical or physical methods. The conditioned matrices according to the invention retain the properties integrated into the matrix by the cultured cells, or by the application of stressors, and are able to deliver the resulting molecular properties of the conditioned matrix when implanted in a host in a manner that more closely simulates the natural state. Thus, the conditioned composition according to the invention supports the replication, differentiation, maturation and spatial organization of cells, therefore augmenting regeneration, replacement, repair, restoration and/or remodeling of an organ or tissue in a patient.

According to one aspect, the invention includes a composition comprising a decellularized matrix. The matrix is conditioned by cells cultured on the matrix in vitro whereby the decellularized conditioned matrix has enhanced restorative, remodeling, replacement or repair properties when placed in contact with a tissue in need of restoration, remodeling, replacement or repair.

In another aspect, the invention provides a composition comprising a matrix. The matrix is conditioned by cells cultured on the matrix in vitro and by exposure to at least one stressor, whereby the conditioned matrix has enhanced restorative, remodeling, replacement or repair properties when placed in contact with a tissue in need of restoration, remodeling, replacement or repair.

The invention further provides a method for inducing restoration, remodeling, replacement, or repair of a tissue in a mammal. The method comprises the steps of providing a decellularized matrix, then conditioning the matrix by culturing cells on the matrix, and lastly, decellularizing the matrix wherein the decellularized, conditioned matrix induces restoration, remodeling, replacement, or repair of the tissue.

In another aspect, the invention includes a composition for tissue replacement, repair, restoration, or remodeling, comprising a decellularized matrix including a structural or functional component of a naturally occurring ECM, a degradation product of a structural or functional component of a naturally occurring ECM, or a combination thereof. The matrix is conditioned by culturing cells on the matrix in vitro.

In yet another aspect, the invention features a composition comprising a matrix and the matrix is conditioned for tissue restoration, remodeling, replacement or repair by exposure to at least one stressor.

According to embodiments of the invention, the matrix, for example, comprises a naturally occurring ECM isolated from the tissues of vertebrates, including, for example, alimentary, respiratory, intestinal, urinary or genital tracts of mammals. In addition, the naturally occurring ECM can comprise at least a portion of tunica submucosa, epithelial basement membrane, tunica propria, or dermis. In other embodiments, the naturally occurring ECM comprises, for example, at least a portion of subcutaneous tissue, respiratory tissue, pancreatic connective tissue, hepatic connective tissue, tissue harvested from the stomach, tissue harvested from the intestine, tissue harvested from the urinary bladder, tissue harvested from the urinary tract, tissue harvested from the liver, tissue harvested from the genital tract, tissue harvested from the skin, or tissue harvested from a tissue comprising a mucous membrane. Alternatively, the naturally occurring ECM comprises a combination of the above, for example, the ECM may comprise tissue harvested from the urinary bladder including a portion of the epithelial basement membrane and a portion of the tunica propria.

Alternatively, in another embodiment, the matrix comprises structural or functional components of naturally occurring ECMs, degradation products of structural or functional components of naturally occurring ECMs, or a combination thereof. The structural or functional components comprise, for example, collagen (i.e., collagen types I-XIX), hyaluronic acid, laminin, fibronectin, elastin, purified components of naturally occurring ECMs, or a combination thereof. Matrixes can include highly conserved collagens, glycoproteins, proteoglycans and glycosaminoglycans in their natural configuration and natural concentration.

According to one embodiment of the invention, cells are cultured on and/or within the matrix, and the cells comprise a primary, secondary and/or immortalized cell population. The cells are, for example, fibroblasts, keratinocytes, astroglial cells, epithelial cells, endothelial cells, glial cells, neural cells, cells of the blood and precursors thereof, and hepatocyte and precursor cells thereof. In a particular embodiment, the cells cultured on and/or within the matrix remain on and/or within the matrix when the matrix is implanted into a host. In another embodiment, primary, secondary or immortalized cells, including autologous cells, are added to a conditioned matrix. These cells can be grown on or within the conditioned matrix and implanted with the conditioned composition at an anatomical site in a patient.

In one embodiment, the cells express a biologically active molecule of interest. The biologically active molecule of interest is produced by the cells and is integrated within the matrix while the cells are cultured on or within the matrix. The biologically active molecule of interest is, for example, a protein, including, for example, a growth factor. The growth factor is, for example, an angiogenic or osteogenic growth factor. In additional embodiments, the protein includes angiogenin, angiopoietin-1, Del-1, acidic-fibroblast growth factor (aFGF), basic-fibroblast growth factor (bFGF), granulocyte colony-stimulating factor (G-CSF), granulocyte-macrophage colony-stimulating factor (GM-CSF), hepatocyte growth factor (HGF), Interleukin-8 (IL-8), leptin, placental growth factor (PlGF), platelet-derived endothelial cell growth factor (PD-ECGF), platelet-derived growth factor-BB (PDGF-BB), pleiotrophin (PTN), proliferin, transforming growth factor-alpha (TGF-alpha), transforming growth factor-beta (TGF-beta), tumor necrosis factor-alpha (TNF-alpha), vascular endothelial growth factor (VEGF), bone morphogenetic protein-2 (BMP-2), and/or stromal derived growth factor-1.

In another embodiment, the cells are genetically modified. In one embodiment according to the invention, the genetically modified cells are transfected cells that comprise an exogenous nucleic acid and that express a protein of interest, or the genetically modified cells are cells transfected with a nucleic acid that encodes a protein of interest. Additionally, the genetically modified cells express one or more biologically active molecules of interest, such as, for example, a VEGF protein, a bFGF protein, a BMP protein, a stromal derived growth factor-1 protein, or a recombinant protein.

Cells cultured on the matrix can also be exposed to at least one stressor or a combination of stressors to enhance the cells' ability to condition the matrix. Exposure to certain stressors can stimulate the release of biologically active molecules from the cells and contribute to the conditioning of the composition for various purposes. Exposure to certain stressors can also prevent the release of undesired biologically active molecules from the cells and contribute to the conditioning of the composition to avoid undesired effects when implanted in a host. According to one embodiment, the stressor is hypoxia, and in another embodiment, the stressor is hypercarbia. Exposure to hypoxia and/or hypercarbia can assist the cells in producing biologically active molecules that are incorporated in the matrix on which the cells are cultured and support, for example, the growth of new blood vessels and assist in the restoration of blood flow to tissue in and surrounding the implantation site. Exposure time to each stressor can vary, for example, from 10 minutes to 1 month, depending on the intended use of the conditioned composition, the type of tissue involved and/or the type of matrix being conditioned.

In other embodiments, the cells are exposed to stressors such as mechanical loading. Exposure to mechanical loading, for example, enhances cellular production of structural proteins and other biologically active molecules, integrating them into the matrix to improve its tensile strength. According to one embodiment, exposure to mechanical loading is achieved by consistently applying strain (i.e., applying a force that causes a change in length) or by applying stress (i.e., applying a mechanical load) to the matrix over a predetermined period of time, for example, for a total time period of 168 hours. Alternatively, mechanical conditioning can be achieved by applying stress or strain to the matrix in a cyclical pattern, for example, applying stress or strain for 1 minute every 5 minutes over a total time of 48 hours. The stress or strain on the matrix is constant throughout the time period, or alternatively, the stress or strain can vary. The amount of stress or strain can vary, for example, from 5% to 15% using an appropriate device, such as a load cell. The stress or strain can be applied in a uniaxial or multiaxial direction. The amount of strain applied can be measured in the cell culture systems by any means known in the art, for example, by laser measurements using laser beams and deflection times.

In another embodiment of the conditioned composition, the cells cultured on the matrix are exposed to an electric current. Exposure to electrical current can, for example, stimulate the release of growth factors and other biologically active molecules from the cell into the matrix, resulting in the matrix exhibiting accelerated tissue regenerative and wound healing properties. The cells are exposed to an electric current for a consistent period of time, or the cultured cells are exposed to an electric current in a cyclical pattern, for example, applying the electric current or electrical potential for 10 seconds every 1 minute over a total time of 1 hour. The electric current potential remains constant over the entire exposure time period, or, alternatively, the magnitude of the electric current potential can alternate between, for example, a positive and negative potential within, for example, a 100 mV-300 mV range.

In another embodiment cells are not cultured on the matrix, and the matrix is exposed to at least one stressor to condition the matrix for its intended use. The stressor can stimulate the release of biologically active molecules or, alternatively, the stressor can be applied to decrease or prevent the release of undesired biologically active molecules into the matrix. The matrix can be exposed, for example, to an electric current or electrical potential. Exposure to electric current or electrical potential can decrease or prevent the release of certain growth factors, such as TGF-beta, from cells existing on the matrix, resulting in a conditioned matrix that decreases the risk of adverse events, such as, for example, the formation of scar tissue, when implanted in a host.

The conditioned composition is useful in replacing, repairing, restoring or remodeling various types of tissue, for example, bone, skin, heart, tissue of the urogenital tract, tissue of the gastrointestinal tract, nervous tissue, joint tissue and connective tissue. The anatomical site in which the conditioned composition will be placed in the body, and/or the other desired physiological effects, e.g., angiogenesis and osteogenesis, play a role in selecting which, if any, cells are cultured on the matrix, as well as which, if any, biologically active molecule is of interest and what, if any, stressor the cells and/or matrix will be exposed to.

For example, the decellularized, conditioned composition can be used to promote vascularization by providing a decellularized scaffold including a matrix conditioned by cells cultured on the matrix that express an angiogenic or vasculogenic protein of interest to the anatomical site in the host requiring vascularization. The decellularized, conditioned composition can also be used, for example, for musculotendinous tissue reconstruction by providing a decellularized composition conditioned with cultured cells that express a structural protein of interest to the anatomical site in the host requiring musculotendinous reconstruction. Additionally, the decellularized, conditioned composition can be conditioned with cells to express a growth factor of interest to stimulate growth of the host's tissues surrounding the composition when that composition is introduced to the anatomical site in the host that is in need of treatment.

The following examples provide further details of practicing the invention. While certain methods useful for practicing the present invention are exemplified below, the invention is not so limited and the skilled artisan will appreciate its wide range of application upon consideration thereof.

EXAMPLE 1

Sources and Preparation of the Matrix

The following provides exemplary methods for preparing a matrix for use according to the invention. A particular example illustrates preparation of a matrix comprising a naturally occurring ECM. Preparation of the naturally occurring ECM for use according to the invention is also described in U.S. Pat. Nos. 4,902,508, 4,956,178, 5,554,389, 6,576,265 and 6,579,538, the entirety of each patent is incorporated by reference herein. For example, intestinal submucosal tissue can be prepared by harvesting tissue from a vertebrate such as porcine, ovine or bovine species. The tissue is subjected to abrasion using a longitudinal wiping motion to remove the outer layers, smooth muscle tissues, and the innermost layer, i.e., the luminal portion of the tunica mucosa. The remaining submucosal tissue or any portion of it is then rinsed with saline.

Alternatively, a naturally occurring ECM including epithelial basement membrane derived from urinary bladder (UBM) can be prepared by removing the urinary bladder tissue from a vertebrate, for example, a pig, and delaminating the tissue by first soaking the tissue in a deepithelializing solution, for example, hypertonic saline, most preferably 1.0 N saline, for periods of time ranging from 10 minutes to 4 hours. Exposure to a hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, submucosa and abluminal portion of the tunica propria are removed from the remaining deepithelialized tissue by mechanical abrasion or by a combination of enzymatic treatment, hydration, and abrasion. Mechanical removal of these tissues is accomplished by removal of mesenteric tissues with, for example, Adson-Brown forceps and Metzenbaum scissors and wiping away the tunica muscularis and abluminal tunica propria using a longitudinal wiping motion with a scalpel handle or other rigid object wrapped in moistened gauze. After these tissues are removed, the resulting ECM consists of epithelial basement membrane and subjacent tunica propria. The tissues may be further processed by rinsing in hypertonic saline, peracetic acid or sterile water. Other methods for removing tissue layers, a microtome, for example, may also be used to obtain the tissue composition of the invention.

Alternatively, the matrix according to the invention comprises a structural or functional component of a naturally occurring ECM, a degradation product of a structural or functional component of a naturally occurring ECM, or a combination thereof. The structural and functional components can include, for example, collagen (i.e., any of collagen types I-XIX), hyaluronic acid, laminin, fibronectin, elastin, purified components of the naturally occurring ECM, or a combination thereof. Matrixes can include, for example, highly conserved collagens, glycoproteins, proteoglycans and glycosaminoglycans in their natural configuration and natural concentration. Methods of preparing a matrix comprising structural or functional components of a naturally occurring ECM and their degradation products are well known in the art, for example, as described in U.S. Pat. Nos. 6,572,650 and 6,051,750, the entirety of each patent is incorporated by reference herein.

The matrix can be stored in a hydrated or dehydrated state. Lyophilized or air dried matrix can be rehydrated and used in accordance with this invention.

In one embodiment, the matrix can be sterilized prior to the addition of cells using conventional sterilization techniques including glutaraldehyde tanning, formaldehyde tanning at acidic pH, propylene oxide treatment, ethylene oxide, gas plasma sterilization, gamma radiation, electron beam, peracetic acid sterilization. Sterilization techniques which do not adversely affect the mechanical strength, structure, and biotropic properties of the tissue are preferred. For instance, strong gamma radiation may cause loss of strength of the sheets of submucosal tissue. Preferred sterilization techniques include exposing the graft to peracetic acid, 1-4 Mrads gamma irradiation (more preferably 1-2.5 Mrads of gamma irradiation) or gas plasma sterilization; peracetic acid sterilization is the most preferred sterilization method. Typically, the tissue is subjected to two or more sterilization processes. After the tissue is sterilized, for example by chemical treatment, the tissue may be wrapped in a plastic or foil wrap and sterilized again using electron beam or gamma irradiation sterilization techniques.

Compositions comprising submucosal tissue can be used for supporting growth or proliferation of eukaryotic cells in vitro. Submucosal tissue can be used in accordance with this invention as a cell growth substrate in a variety of forms, including its naturally occurring sheet-like configuration, as a gel matrix, as an addition for art-recognized cell/tissue culture media, or as coating for culture-ware to provide a more physiologically relevant substrate that supports and enhances the proliferation of cells in contact with the matrix. The submucosal tissue provides surfaces for cell adhesion and also helps induce cell differentiation.

While the matrix is preferably sterilized prior to the addition of cells, nonsterile matrix can be used if antibiotics are included in the cell culture system.

The matrix can be decellularized after cells have been cultured on the matrix using any technique known in the art. For example, the matrix can be decellularized by placing the matrix in a decellularizing solution such as in hypertonic saline, for example, 1.0N saline or in Hanks buffered saline solution (HBSS).

After the matrix has been conditioned according to embodiments of the invention, primary, secondary or immortalized cells, including autologous cells, can be added to and grown on and/or within the conditioned matrix and implanted with the conditioned composition at an anatomical site in a patient. The type of primary, secondary, and/or immortalized cell is chosen based upon the intended use of the conditioned composition, the anatomical site of implantation of the conditioned composition or the desired physiological properties of the conditioned composition.

EXAMPLE 2

Sources and Preparation of Cells

The following provides exemplary sources and methods for the preparation of matrix conditioning cells that may be cultured on the matrix to make the conditioned matrix according to the invention. The composition and configuration of the matrix provides a unique cell growth substrate that promotes the attachment and proliferation of various types of cells. Generally, methods involve contacting the cells with the matrix under conditions conducive to cell growth and which are well known in the art.

The matrix conditioning cells can be prokaryotic or eukaryotic cells such as vertebrate cells (particularly mammalian cells, such as cells derived from a human, chimpanzee, mouse, rat, hamster, guinea pig, rabbit, cow, horse, pig, goat, sheep, dog, or cat). The matrix conditioning cells can be primary cells, secondary cells, and/or immortalized cells, and the matrix conditioning cells can be autologous cells. The types of matrix conditioning cells include fibroblasts, keratinocytes, epithelial cells (e.g., mammary epithelial cells, intestinal epithelial cells), endothelial cells, adipocytes, astrocytes, cardiac muscle cells, chondrocytes, glial cells, neural cells formed elements of the blood (e.g., lymphocytes, bone marrow cells), muscle cells, gangliocytes, glandular cells, glial cells, hematopoietic cells, mesenchymal cells, hepatocytes and precursors of these somatic cell types.

Additionally, the matrix conditioning cells can be genetically modified cells. Various genetically modified mammalian host cell lines can be used, for example, L cells, C127, 3T3 fibroblasts, T-84 cells, Chinese hamster ovary (CHO), HeLa, BHK cell lines, CV-1 cells (ATCC CCL70), COS-7 cells and CV-1/EBNA. A matrix conditioning cell of choice can be genetically modified by transducing into the cell exogenous nucleic acid sequences. The exogenous nucleic acid can encode a biologically active molecule of interest, such as a protein, or alternatively, the exogenous DNA can be a regulatory sequence that will activate expression of an endogenous gene (for example, using homologous recombination) to produce a biologically active molecule of interest. These techniques are well known and may be found in, e.g., Sambrook et al. (1989) Molecular Cloning: A Laboratory Manual (2d ed., Cold Spring Harbor Laboratory Press, Plainview, N.Y.) and other laboratory manuals.

EXAMPLE 3

Biologically Active Molecules of Interest

Any desired biologically active molecule can be selected for secretion onto the matrix. The biologically active molecule of interest is chosen based on where the conditioned composition is to be located in the body and/or the physiological requirements of the recipient. For example, if the decellularized, conditioned composition is used to repair bone, the biologically active molecule of interest which is produced on the matrix can be a bone growth factor, such as a bone morphogenic protein, e.g., BMP-2. The biologically active molecule of interest can include enzymes, hormones, cytokines, colony stimulating factors, vaccine antigens, antibodies, clotting factors, angiogenesis factors, regulatory proteins, transcription factors, receptors, and structural proteins, for example, epithelial basement membrane proteins such as type IV collagen, laminin, and fibronectin. The biologically active molecule of interest can also include human growth hormone, Factor VIII, Factor IX, erythropoietin, and insulin. For genetically modified cells, nucleic acid sequences and amino acid sequences for biologically active molecules of interest can be readily obtained from National Center for Biotechnology Information. (http://www.ncbi.nlm.nih.gov/).

In a particular example, a biologically active molecule of interest is expressed in the genetically modified matrix conditioning cell using an expression vector such as a mammalian expression vector. Mammalian expression vectors typically contain non-transcribed elements such as an origin of replication, a suitable promoter, such as, for example, the ROSA promoter, and an enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. The transcriptional and translational control sequences in expression vectors to be used in transforming vertebrate cells may be provided by viral sources. Commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of an exogenous DNA sequence. The early and late promoters are particularly useful because both are obtained easily from the virus as a fragment that also contains the SV40 viral origin or replication.

For secretion of the biologically active molecule of interest, for example, a protein of interest, the expression vector may comprise DNA encoding a signal or leader peptide such as the native signal sequence of IL-7 or interleukin-4.

The biologically active molecule of interest can include a recombinant protein. High-yield production of recombinant proteins can be produced by cells that stably express a protein of interest. Cell lines which stably express the protein of interest may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker.

Vector DNA can be introduced into eukaryotic matrix conditioning cells via conventional transduction techniques such as using calcium phosphate or calcium chloride co-precipitation, DEAE-dextran-mediated transfection, lipofection, or electroporation.

Following the introduction of the exogenous DNA, engineered matrix conditioning cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. Preferred selectable markers include G418, hygromycin and methotrexate. Such engineered cell lines can then be added to the matrix and cultured, and a biologically active molecule of interest can be secreted onto and integrate into the matrix.

EXAMPLE 4

Culturing Cells on the Matrix

Matrix conditioning cells can be cultured, in vitro, on and/or within the matrix, using a matrix prepared by any of the methods described above. The cells are cultured under conditions conducive to cell growth and if desired, under conditions conducive to expression of a biologically active molecule of interest. Conditions for cell culturing are well known in the art and are dependent on the particular cell type. While not wishing to be bound by theory, it is believed that a biologically active molecule that is expressed by matrix conditioning cells on the matrix, in vitro, is incorporated into the matrix similar to the manner by which molecules, such as proteins, are integrated into a naturally occurring extracellular matrix in vivo. The incorporation of the molecule produced by the cultured cells into the matrix imparts superior restorative properties to this conditioned composition compared to the mere addition of, for example, a protein to a decellularized matrix. It is believed that the incorporated biologically active molecule is released in the recipient of the conditioned composition as a function of composition degradation. Additionally, the conditioned composition can be substantially devoid of cellular elements that may lead to rejection of the tissue implant by the recipient.

EXAMPLE 5

Uses of the Conditioned Composition of the Invention

The composition of the invention can be implanted into any anatomical location in the body of the host where there exists a tissue in need of regeneration, repair, replacement, restoration or remodeling.

A. Conditioned Composition for Enhanced Vascularization

Angiogenesis and vasculogenesis are an integral part of the restoration of blood flow to transplanted tissue. The process of angiogenesis involves the migration and proliferation of capillary endothelial cells in the early post-injury phase, and the differentiation of the capillary endothelial cells in the later post-injury phase to organize endothelial cells into a microvascular network. Angiogenesis requires dynamic interactions between cells such as fibroblasts, epithelial and endothelial cells, and a wide array of angiogenic and vasculogenic factors and cytokines that exist within the matrix, such as FGF, VEGF, TGFβ, and others. These cells and matrix composites orchestrate the proliferative, inhibitory, and differentiation phases of cells to re-populate, repair and restore damaged tissues and its vascular supply.

The following experiment relates to the use of the conditioned composition of the invention in relation to vasculogenesis and myelogenesis. A naturally occurring ECM derived from urinary bladder was cultured with matrix conditioning transfected cardiac myofibroblasts that constitutively express SDF-1. SDF-1 concentration in the media and in the matrix was measured over a six day time period. Results showed that the concentration of SDF-1 in the scaffold increased more than 100 fold in just six days (from less than 5 pg/ml to 625 pg/ml).

The SDF-1 conditioned matrix was decellularized as described above and implanted subcutaneously into mice that have been genetically altered to express green fluorescent protein in all bone marrow-derived cells. Control mice were similarly treated using non-conditioned naturally occurring ECM or simply a sham operation. Blood vessel formation in the mice was measured and quantified by performing morphometric assays on cross sectional samples taken from predetermined sites in low magnification fields. Following 7 and 14 days, mice treated with the decellularized, conditioned scaffold of the invention had increased blood vessel formation and increased numbers of bone marrow-derived cells compared with control mice. Results demonstrated a percentage increase in blood vessel cross sectional area of 48%+/−13%, $p<0.05$ compared to a control (non-conditioned) matrix.

According to exemplary methods, the conditioned compositions of the invention are used to improve angiogenesis in the composition after implantation. Exposure of the matrix conditioning endothelial cells to a hypoxic environment assists the matrix conditioning cells in releasing a natural complement of angiogenic factors into the matrix that will enhance the matrixes specificity. The period of exposure time can range from one minute to thirty minutes. Such angiogenesis and vasculogenesis factors can include one or more of the following proteins: FGF, VEGF, TGFβ, and Angiopoietin. The matrix is decellularized but retains the angiogenic factors that have become integrated in the matrix. The conditioned matrix is then implanted within a recipient in need of vascular assistance and results in enhanced vascularization properties in vivo.

In a particular experiment, a naturally occurring ECM was prepared as explained above. Matrix conditioning endothelial cells (EC) were delivered to the matrix and cultured on the matrix under normoxic conditions for a period of 72 hours, with the last 24 hours in serum-free media. The cultured cells were then exposed to a hypoxic environment having 2% oxygen for a period of 48 hours. The concentration of the 165 and 189 isoforms of VEGF protein was measured in both the matrix and the supernatant. Results showed a 5-fold increase of VEGF concentration in the matrix and a 10-fold increase of VEGF in the supernatant as compared to a control in which EC cells were cultured under the same conditions but not exposed to a hypoxic environment.

One illustrative experiment pertains to use of the invention in regenerating heart tissue. A naturally occurring ECM derived from the small intestine measuring approximately 1 cm×2 cm is prepared as described above and is seeded with matrix conditioning fibroblasts at 0.5×106 cells/cm². The matrix conditioning fibroblasts are genetically engineered to express stromal derived growth factor-1 (SDF-1). The matrix conditioning genetically modified cells are cultured with the matrix during a time period ranging from 24 to 168 hours. The presence of SDF-1 in the conditioned matrix is determined by ELISA. The matrix is then decellularized by placing the matrix in HBSS. Following decellularization, the conditioned matrix is implanted by a surgical procedure to a damaged area of the myocardium in the recipient. As the decellularized, conditioned composition is degraded by the recipient, the protein of interest, for example, SDF-1, is released along with other products of matrix degradation. Thereafter, the conditioned composition attracts circulating multi-potential cells that are influenced, for example, to differentiate towards cardiomyocytes. The period of exposure time can range from one minute to thirty minutes.

In another illustrative example, a naturally occurring ECM is prepared as described above and is seeded with matrix conditioning cells that are genetically modified to produce factors which improve angiogenesis and/or vasculogenesis. Such angiogenesis and vasculogenesis factors can include one or more of the following proteins: FGF, VEGF, TGFβ, and Angiopoietin. After a suitable incubation period, the matrix is decellularized by methods described above. After decellularization, the conditioned composition is implanted at a location in the host that is in need of new blood vessel formation, for example, into heart tissue for the treatment of ischemic myocardium caused by, for example, a myocardial infarct.

Although the examples provided above refer to the use of a naturally occurring ECM, the experiments can also be performed using a matrix comprising structural or functional components of a naturally occurring ECM and/or degradation products thereof.

B. Conditioned Composition for Enhanced Strength

The following is an exemplary method for using the invention to enhance the strength of a composition for tissue repair, replacement, restoration or remodeling. The matrix is prepared as explained above, and matrix conditioning fibroblast cells are introduced to the matrix and exposed to mechanical loading. A cyclic loading system that allows for independent control of stress and strain is applied to the matrix in a bioreactor environment and a cell culture system provides for sterile conditions while simultaneously monitoring the stress and strain load in the matrix. The cell culture system includes, for example, a load cell with 25 N capacity and a linear actuator with a 30 mm travel capacity. The system allows the user to apply a load to each matrix and define the displacement profile by specifying the amplitude and frequency of oscillation or by defining a function to prescribe the displacement. Exposure of the matrix and/or matrix conditioning fibroblast cells to mechanical loading assists in the release of structural proteins and other biologically active molecules from the cells and into the matrix. The conditioned composition including the matrix is decellularized prior to implantation in a host.

In one illustrative example, a matrix comprising a naturally occurring ECM is prepared as described above and genetically modified cells that secrete structural proteins, such as collagen, after a suitable incubation period are cultured on the matrix. The matrix is decellularized prior to implantation into a host to form the conditioned composition according to the invention.

In a particular example, $0.5 \times 10^6$ cm² of fibroblasts were introduced to a naturally occurring ECM derived from the small intestine measuring approximately 1 cm×2 cm. The cells were cultured on the matrix for approximately 12 hours, during which time a preload amount of 0.25 N was applied. A strain of 10% was then applied to the matrix at 1 Hz for 24 hours. The load placed upon the matrix was monitored continuously during the experiment, and the cell number and pH of the media were determined at the conclusion of the experiment. Cell viability was determined using the MTT assay to stain metabolically active cells. The presence of procollagen Type I was determined with the use of an ELISA kit. Results showed that the fibroblasts rapidly aligned along the lines of applied stress and assumed an elongated, spindloid morphology. Such results indicate that the strength of the conditioned composition will be enhanced compared to compositions not similarly conditioned when implanted in a host.

The experiments described above can also be performed using a matrix comprising structural or functional components of a naturally occurring ECM and/or degradation products thereof.

C. Conditioned Composition for Bone Formation

In another illustrative example, the conditioned composition of the invention is used to promote bone formation. A matrix comprising a naturally occurring ECM is prepared as described above. Matrix conditioning genetically modified cells that secrete the bone growth factor, bone morphogenetic protein-2 (BMP-2), are cultured on the matrix for a suitable incubation period. The matrix is then decellularized prior to implantation into a host. The same experiment can be performed using a matrix comprising structural or functional components of a naturally occurring ECM.

D. Conditioned Composition for Inducing Growth of a Tissue

According to the following exemplary method, a matrix comprising a naturally occurring ECM is prepared as described above and matrix conditioning cells that produce growth factors and other biologically active molecules after a suitable incubation period are cultured on the matrix. The cultured cells are exposed to either constant or alternating electrical potential for the purpose of stimulating the release of growth factors and other biologically active molecules from the cells into the matrix prior to implantation. In one illustrative example, the matrix is seeded with a population of matrix conditioning endothelial cells prior to its exposure to electrical potential. An electric potential in the range of 25 mV to about 500 mV, preferably 300 mV, is applied across the matrix for 24 hours to 72 hours, preferably for 48 hours. Upon the cells exposure to electric current, growth factors and other biologically active molecules, such as, for example, proteins, enzymes, hormones, and cytokines, are released from the cells and are incorporated into the matrix. The matrix is then decellularized prior to its implantation into the host. The method can also be performed using a matrix comprising structural or functional components of a naturally occurring ECM and/or degradation products thereof.

Scattered reports exist that applied electrical potential can facilitate various forms of wound healing. Applying low level electrical potential to severely ischemic tissue in the rabbit has been reported to accelerate healing and promote neovascularization of the tissue. Chekanov et al. (2002), Electrical stimulation promotes angiogenesis in rabbi hind-limb ischemia model, Vasc. Endovascular Surg. Vol. 36, pp. 357-366. Electrical potential has been used to accompany acupuncture treatment of wounds and to treat non-healing bone fractures, ulcers and to stimulate nerve regeneration. Sisken et al. (1993), Prospects on clinical applications of electrical stimulation for nerve regeneration, J. Cell Biochem., vol. 51, pp. 404-409; Evans et al. (2001), Electrical stimulation with bone and wound healing, Clin. Podiatr. Med. Surg., vol. 18, pp. 79-95. Data suggests that in these studies, the applied electrical potential stimulates the release of biologically active factors in vivo, either from cells, from the matrices or from both.

E. Conditioned Composition for Reducing Undesired Properties

According to the following exemplary method, a matrix comprising a naturally occurring ECM is prepared as described above. The matrix is exposed to an electric potential that depletes the matrix of certain biologically active molecules that can result in undesired properties when the matrix is implanted in a host. In one particular example, the matrix is exposed for a period of 72 hours to a constant electric current potential known to reduce or prevent the release of TGF-beta growth factors. The conditioned matrix is then implanted in a host and the risk of undesired scar tissue formation at the site of implantation is decreased.

F. Conditioned Composition for Tissue-Specific Compatibility

According to the following illustrative method, a matrix comprising a naturally occurring ECM is prepared as described above and conditioned in vitro by the addition of a specific population of matrix conditioning cells, such as astroglial cells, chosen to bestow upon the matrix characteristics known to be unique to the naturally occurring ECM of a particular tissue type, such as tissues of the central nervous system (CNS). In one example, matrix conditioning hepatocytes are introduced and cultured on the matrix to confer upon it the properties inherent to the naturally occurring ECM that surrounds liver tissue. The cultured cells are removed before implantation into a recipient. The decellularized conditioned matrix can direct endothelial cell differentiation, for example, hepatic sinusoidal endothelial cell (HSEC) differentiation and brain endothelial cell (BEC) differentiation, upon transplant of the conditioned matrix into the target tissue of the host. The method can also be performed using a matrix comprising structural or functional components of a naturally occurring ECM and/or degradation products thereof.

A naturally occurring ECM is a dynamic structure that reflects the products of the resident cells and is tissue and organ specific. The composition conditioned according to the exemplary methods described above comprises a specialized matrix, in that, once decellularized, the matrix maintains the properties associated with the cellular subtypes present during the conditioning and/or culturing phase. The conditioned composition can be primed for implantation into a target region and will demonstrate improved restorative capabilities as compared with an unconditioned matrix. Endothelial cells (EC), for example, show diverse phenotypic potential. EC phenotype is related to EC function, and function is site dependent. For example, renal glomerular endothelial cells are well-suited for a glomerular filtration function. Hepatic sinusoidal endothelial cells have the unique phenotypic characteristic of fenestrations or "sieve plates" that are essential for normal hepatic blood filtration functions. Alternatively, endothelial cells in the brain are a critical component of the blood-brain barrier that is virtually impermeable to most molecules. Vascular networks within the CNS have no fenestrations (i.e., blood-brain barrier) and express zona occludens 1, 2 and 3 proteins characteristic of tight junctions.

Variations and modifications of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method for conditioning a decellularized composition, comprising:
   (i) exposing cultured epithelial cells to a stressor selected from the group consisting of a mechanical stimulus, an electrical stimulus, hypoxia, and hypercarbia to condition said epithelial cells;
   (ii) providing a naturally-occurring matrix comprising native epithelial cells and structural components of an extracellular matrix arranged in their native orientation obtained from an epithelial tissue of a mammal;

(iii) decellularizing the naturally-occurring matrix to remove said native epithelial cells; then (iv) conditioning the decellularized matrix by culturing said conditioned epithelial cells on the decellularized matrix; followed by (v) decellularizing the conditioned matrix to remove the conditioned epithelial cells.

2. The method of claim 1 wherein said epithelial cells are derived from a species selected from the group consisting of chimpanzee, mouse, rat, hamster, guinea pig, rabbit, cow, horse, pig, goat, sheep, dog, human, and cat and said naturally occurring matrix is derived from a species selected from the group consisting of pig, sheep, and cow.

3. The method of claim 1 wherein the conditioned epithelial cells are genetically-modified cells.

4. The method of claim 1 wherein the at least one stressor comprises exposing said cells to mechanical loading in a uniaxial or multiaxial direction, wherein mechanical loading is selected from the group consisting of a continuous application of loading by strain, a continuous application of loading by stress, a cyclical application of loading by strain, and a cyclical application of loading by stress; and, optionally, wherein the stress or strain varies by 5% to 15%.

5. A method for manufacturing a decellularized conditioned composition for inducing restoration, remodeling, replacement or repair of a tissue in a patient, the method comprising: conditioning epithelial cells of interest by exposing the epithelial cells to at least one stressor selected from the group consisting of a mechanical stimulus, an electrical stimulus, hypoxia and hypercarbia;

providing a naturally-occurring matrix obtained from an epithelial tissue of a mammal comprising structural components of an extracellular matrix arranged in their native orientation; then decellularizing the naturally-occurring matrix to remove native cells; then conditioning the decellularized matrix by culturing said conditioned epithelial cells on the decellularized matrix in vitro; followed by decellularizing the conditioned matrix to remove the conditioned epithelial cells thereby forming the decellularized conditioned composition that induces restoration, remodeling, replacement or repair of the tissue.

6. The method of claim 5 wherein said epithelial cells are derived from a species selected from the group consisting of chimpanzee, mouse, rat, hamster, guinea pig, rabbit, cow, horse, pig, goat, sheep, dog, human, and cat and said naturally occurring matrix is derived from a species selected from the group consisting of pig, sheep, and cow.

7. The method of claim 5 wherein the conditioned epithelial cells express a biologically active molecule of interest selected from the group consisting of VEGF protein, a stromal derived growth factor-1 protein, a bone morphogenic protein, and combinations thereof.

8. The method of claim 5 wherein the conditioned epithelial cells express SDF-1.

9. The method of claim 5, wherein said conditioned epithelial cells express a an osteogenic growth factor.

10. The method of claim 5 wherein said conditioned epithelial cells express a biologically active molecule of interest selected from the group consisting of angiogenin, angiopoietin-1, Del-1, acidic-fibroblast growth factor (aFGF), basic-fibroblast growth factor (bFGF), granulocyte colony-stimulating factor (G-CSF), granulocyte-macrophage colony-stimulating factor (GM-CSF), hepatocyte growth factor (HGF), interleukin-8, leptin, placental growth factor (F1GF), platelet-derived endothelial cell growth factor (PD-ECGF), platelet-derived growth factor-BB (PDGF-BB), pleiotrophin (PTN), proliferin, transforming growth factor-alpha (TGF-alpha), transforming growth factor-beta (TGF-beta), tumor necrosis factor-alpha (TNF-alpha), vascular endothelial growth factor (VEGF), bone morphogenic protein-2 (BMP-2), stromal derived growth factor-1, and combinations thereof.

11. The method of claim 5 wherein the conditioned epithelial cells are genetically-modified cells.

12. The method of claim 11 wherein the conditioned genetically-modified epithelial cells express SDF-1.

13. The method of claim 11 wherein said genetically-modified cells are transfected with an exogenous nucleic acid.

14. The method of claim 5 wherein the at least one stressor comprises exposing said cultured epithelial cells to mechanical loading in a uniaxial or multiaxial direction, wherein mechanical loading is selected from the group consisting of the continuous application of loading by strain, the continuous application of loading by stress, the cyclical application of loading by strain, and the cyclical application of loading by stress; and, optionally, wherein the stress or strain varies by 5% to 15%.

15. The method of claim 5 wherein the tissue requiring restoration, remodeling, replacement or repair comprises heart tissue.

* * * * *